United States Patent [19]

Ellis

[11] Patent Number: Plant 7,598

[45] Date of Patent: Jul. 23, 1991

[54] FRAGARIA 'FREL'

[75] Inventor: Jack R. Ellis, Bourne End, England

[73] Assignee: Blooms of Bressingham Ltd., Norfolk, England

[21] Appl. No.: 418,436

[22] Filed: Oct. 6, 1989

[51] Int. Cl.[5] ..... A01H 5/00

[52] U.S. Cl. ..... Plt./48

[58] Field of Search ..... Plt./54, 48, 49

*Primary Examiner*—Howard J. Locker

*Attorney, Agent, or Firm*—Keith D. Gehr

[57] ABSTRACT

An ornamental cultivar of Fragaria characterized by continuous flowering with beautiful pink blooms.

1 Drawing Sheet

The present invention relates to a new and distinct hybrid of Fragaria which originated as a cross-pollination of *Fragaria*×*anassa* (*Fragaria grandiflora*) and *Potentilla palustris* in the Rosaceae family.

This new Fragaria is the result of a controlled breeding program conducted at Bucks, England. This new hybrid was selected for further evaluation from the fifth backcross due to its unique pink flower color and other outstanding characteristics. The variety has been reproduced by asexual propagation (runners). Each of the progeny exhibits identical characteristics to the original mother plant, establishing this hybrid as reproducible and true to type. The plant will not reproduce from seed.

The present cultivar is designated Fragaria because it is a chromosome addition line of the cultivated strawberry and is 96% Fragaria. It most closely resembles Fragaria in foliage and habit and does produce strawberry-type fruits. The distinctive characteristic of 'Frel' is the flower color which is deep pink. This is unique for a strawberry plant which normally produces white flowers.

The new hybrid is unlike any Fragaria commercially available nor like any of those described by Bailey, Blooms or others (see reference list) as evidenced by the following unique characteristics:

1. Succession of bright pink flowers and very little fruit from spring well into autumn.
2. Vigorous plant with bright green foliage throughout all but the harshest of winters.

BRIEF DESCRIPTION OF THE PHOTOGRAPH

The single FIGURE is a photograph showing a container planting of the new variety and indicating the vigorous growth with bright green foliage and an abundance of flowers.

DETAILED PLANT DESCRIPTION

The following is a detailed description of the new Fragaria hybrid based on observations of specimen plants grown in Bressingham, England and Federal Way, Wash. The color determinations are all based on The Royal Horticultural Society Colour Chart.

Overall Size and Growth Habit

Size: The ultimate size of the new variety is 10 to 20 cm (4 to 8 inches) tall and a spread of 15 to 20 cm (6 to 8 inches). The Fragaria is a herbaceous perennial which spreads by runners and can be used as a ground cover, pot plant or hanging basket.

Foliage:

*Type.*—Semi-evergreen leaves which will die back to ground in severe winters.

*Shape.*—Obovate.

*Length.*—2.5–5 cm (1 to 2 inches).

*Width.*—2–4 cm (¾ to 1.5 inches).

*Petiole length.*—5–7 cm (2 to 3 inches).

*Margins.*—Coarsely serrate.

*Apex.*—Obtuse.

*Base.*—Cuneate.

*Texture.*—Smooth, glossy upper surface; hairy lower surface.

*Leaf arrangement.*—Compound with three leaflets.

Flower:

*Petal count.*—6 to 7.

*Petal shape.*—Orbicular.

*Flower type.*—Complete; Simple.

*Flower size.*—2.5 to 3.5 cm (1 to 1.5 inches).

*Blooming habit.*—Cyme which is slightly taller than foliage.

*Bloom period.*—Late April through mid-November.

Color Characteristics

Foliage:

*Mature leaves upper surface.*—R.H.S. Colour Chart Fan 3, Green Group, No. 137A.

*Mature leaves lower surface.*—R.H.S. Colour Chart Fan 3, Green Group, No. 138D.

Flowers:

*Petals.*—R.H.S. Colour Chart Fan 2, Red-Purple Group No. 68C.

*Carpels.*—R.H.S. Colour Chart Fan 1, Yellow Group No. 13B.

*Stamens.*—R.H.S. Colour Chart Fan 1, Yellow Group No. 13B.

Fruit:

*Size.*—2 cm in diameter and 2 cm in length.

*Shape.*—Round.

*Quantity.*—About 20–30 fruits per plant.

*Color.*—Early fruits are white with dark green seeds carried on the outside skin of the fruit. The fruits turn a glossy scarlet and then turn dark crimson with dark brown seeds.

*Season.*—Fruits are produced more or less continuously with the blooming period according to seasonal conditions. More fruits are produced in hot weather.

DESCRIPTION OF PARENTS AND SIMILAR PLANTS

This Fragaria cultivar hybrid has characteristics which make it unique from either of its parents: *Fragaria grandiflora* and *Potentilla palustris.*

*Fragaria*×*anassa* is characterized as a fruiting strawberry with white flowers. It usually has one flush of flowers followed by fruit.

*Potentilla palustris* is described in Hortus as having five to seven leaflets on each stem and a plant size of about 45 cm (18 inches). Flowers range in color from red to purple. The main contribution of the Potentilla parent to the hybrid appears to be the pink flower color, continuous blooming and increased petal count.

References

1. Bailey, L. H. and E. Z. Bailey. 1976. *Hortus Third.* McMillian. New York.
2. Blooms of Bressingham. 1989. *Bressingham Gardens Autumn Catalog,* 1989. Diss, England.

I claim:

1. A new and distinct cultivar of Fragaria substantially as shown and described, characterized by: continuous flower from spring through fall with bright pink flowers and very little fruit on a plant that is very hardy with bright semi-evergreen leaves.

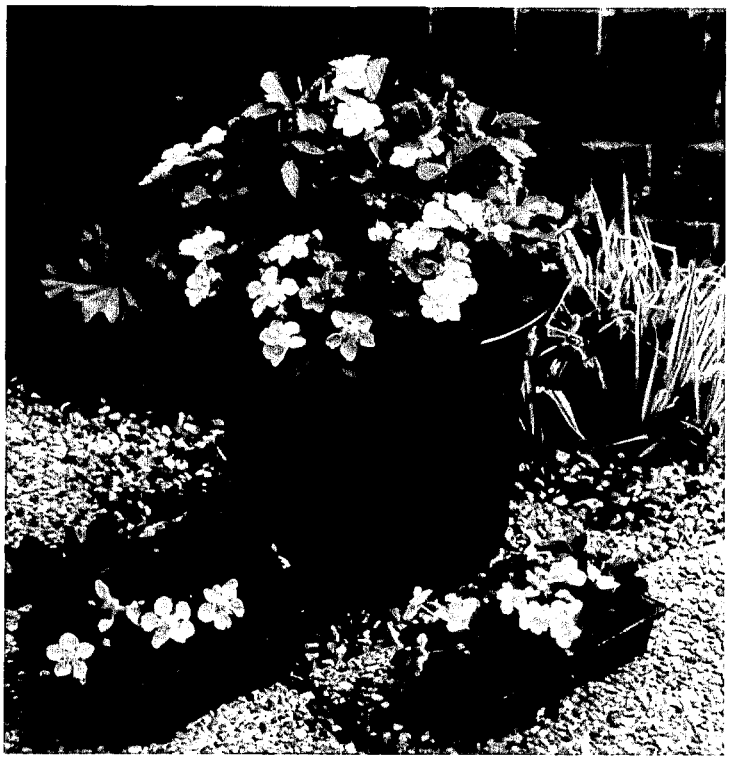

* * * * *